US00PP35063P2

(12) United States Plant Patent
Hansen

(10) Patent No.: US PP35,063 P2
(45) Date of Patent: Mar. 21, 2023

(54) ***HELIOPSIS* PLANT NAMED 'BIT OF HONEY'**

(50) Latin Name: ***Heliopsis helianthoids* (L.) Sweet**
Varietal Denomination: 'Bit of Honey'

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,303

(22) Filed: Apr. 28, 2022

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 5/02
See application file for complete search history.

*Primary Examiner* — Kent L Bell

(57) ABSTRACT

The new and distinct hardy perennial plant, *Heliopsis* 'Bit of Honey', has dense, rounded, mound habit with extensively-branched, predominately strong upright stems that resist lodging. The foliage is narrowly ovate to broadly lanceolate with green surrounding the veins and near white between the veins. Inflorescences are in a capitulum with two or three whorls of golden-yellow, overlapping, ray florets and central disk florets of gold coloration. The new plant is freely flowering and begins blooming in early summer and continues for about six weeks. The new plant is useful in the landscape en masse, as an accent, in containers or as cut flowers.

1 Drawing Sheet

Botanical denomination: *Heliopsis helianthoides* (L.) Sweet.

Variety designation: 'Bit of Honey'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. was on Dec. 1, 2021. The claimed plant was first sold on Aug. 23, 2021 to Corsos Flower and Garden Center as well as other nurseries afterward by Walters Gardens, Inc., who obtained the plant and all information relating from the inventor. No plants of *Heliopsis* 'Bit of Honey' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to a new and distinct cultivar of *Heliopsis* 'Bit of Honey'. The new plant was selected as a single seedling from the progeny of a cross by the inventor between 'Tuscan Sun' U.S. Plant Pat. No. 18,763 as the female or seed parent and 'Sunstruck' U.S. Plant Pat. No. 25,524 as the male or pollen parent on Jul. 7, 2015. Seed was harvested in the fall of 2015 and eventually assigned the breeder code 15-5-21 toward the end of the trial period. 'Bit of Honey' was approved in a final evaluation in the summer of 2019 and slated for later introduction. The new plant was selected based on the compact habit, strong stems, ability to withstand lodging, mildew resistance, attractive foliage, high-quality flowers over a long period, and ability to attract pollinators. The new plant has been asexually first propagated by division and later by shoot tip cuttings with the resultant plants remaining identical to the original plant, stable and true to type in successive generations.

SUMMARY OF THE INVENTION

Plants of the new *Heliopsis* have not been observed under all possible combinations of environmental conditions and cultural practices. The phenotype may vary somewhat with variations in environmental conditions comprising temperature, daylength, light intensity, and fertility, without, however, any variance in genotype.

The following traits have been repeatedly observed and are determined to be the unique characteristics of the new *Heliopsis* plant. These characteristics in combination distinguish 'Bit of Honey' as a new and distinct *Heliopsis* plant:

1. Foliage with green directly surrounding the veins and near white between the veins;
2. Dense rounded mound plant habit;
3. Extensive branching habit;
4. Freely flowering habit beginning in early summer and continuing for about six weeks;
5. Large inflorescences with multiple rows of golden-yellow ray florets and deeper gold disk florets;
6. Ray florets held above slightly outwardly to upwardly;
7. Strong garden performance.

The female parent has a taller and more upright habit with solid, non-variegated, green foliage. The male parent has foliage that has green veins and white between the veins with a shorter habit than the new plant. The male parent has fewer ray florets per inflorescence, and they are more yellow and less gold and held more horizontally.

The following cultivars are the most similar cultivars known to the inventor: 'Loraine Sunshine' U.S. Plant Pat. No. 10,690, 'Summer Green' U.S. Plant Pat. No. 23,410, 'Sunstruck' U.S. Plant Pat. No. 25,524, 'Double Sunstruck' U.S. Plant Pat. No. 26,608, and the seed variety 'Sunburst' (not patented).

'Loraine Sunshine', 'Summer Green', and the seed variety 'Sunburst' are all taller and more upright in habit but have similar variegated foliage. 'Summer Green' also has much darker purple stems. 'Sunstruck' has a shorter more compact habit with similar variegated foliage. 'Double Sunstruck' has more ray florets, weaker stems that have a greater tendency to lodge. 'Bit of Honey' has more ray florets that overlap more than all of the above comparison cultivars except 'Double Sunstruck'.

BRIEF DESCRIPTION OF THE DRAWINGS

The photographs of the new plant demonstrate the unique traits of *Heliopsis* 'Bit of Honey' and the overall appearance of a three-year-old plant in the full sun display garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
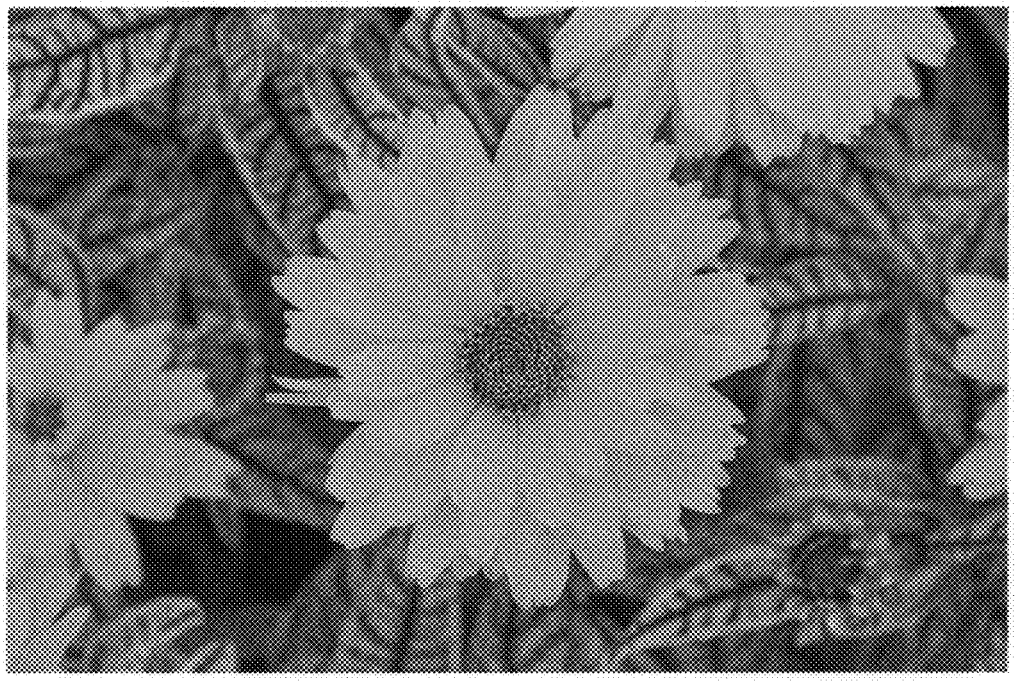
FIG. 1 shows a close-up of the inflorescence and bud from above.
Figure 2:
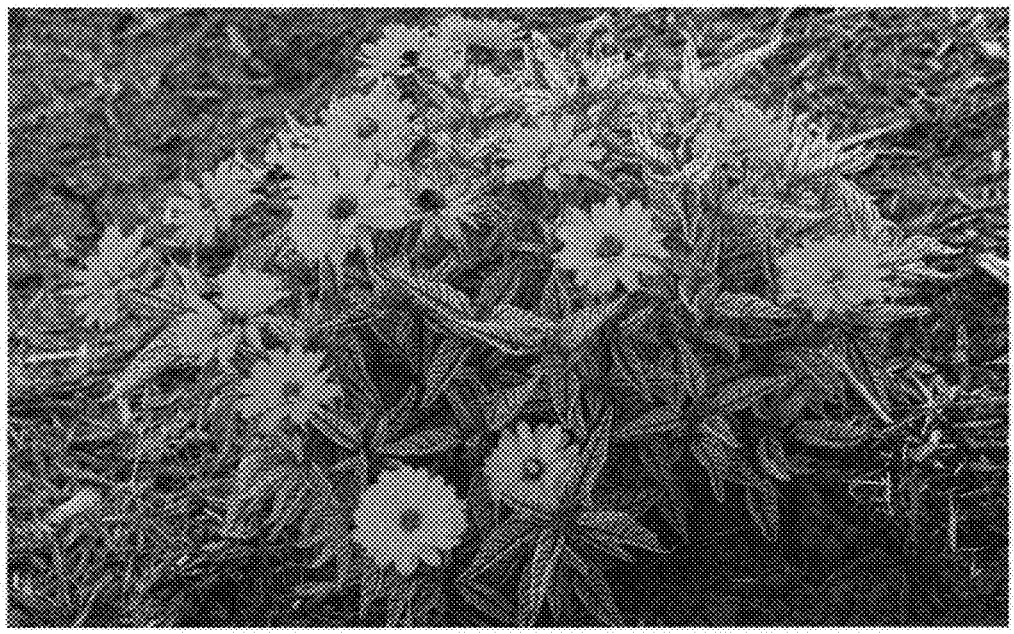
FIG. 2 shows the landscape habit of the new plant.

The following descriptions and color references are based on the 2015 edition of The Royal Horticultural Society Colour Chart except where common dictionary terms are used. *Heliopsis* 'Bit of Honey' has not been observed under all possible environments. The phenotype may vary slightly with different growing environments such as temperature, light, fertility, soil pH, moisture, and maturity levels, but without any change in the genotype. The following observations and size descriptions are based on three-year-old plants grown in a trial garden and a partially shaded greenhouse at a nursery in Zeeland, Mich. with supplemental fertilizer and water as needed and without growth regulators or pinching.

Botanical classification: *Heliopsis helianthoides;*

Parentage: The female (seed) parent is 'Tuscan Sun'; the male (pollen) parent is 'Starstruck';

Plant habit: Multi-stemmed, heavily-branched, herbaceous perennial forming a dense rounded mound;

Propagation: Shoot tip cuttings;

Plant size: To about 45 cm tall and 50 cm wide;

Time to initiate roots: About one to two weeks;

Growth rate: Moderate; about 8 to 12 weeks to finish in a 3.8-liter container from a rooted 25 mm plug liner;

Root description: Fibrous; medium thickness; light tan to white in color, depending on soil composition, water quality, fertilizer type and formulation, substrate temperature, and physiological age of roots; medium density;

Stems: To about 15 per plant; cylindrical; micro-puberulent; to about 44 cm length and 6 mm diameter at base;

Stem color: Proximally nearest RHS 146D and distally nearest RHS 146B;

Branches: About 6 branches per stem beginning about 19 cm above soil; cylindrical; micro-puberulent; strong; flexible; to about 16 cm long and 2 mm diameter at base; color nearest RHS 146B;

Branch aspect: About 45 degrees above horizontal;

Nodes: About 7 below branches and a total of 13 to 15 before flowers; average internode length about 3.1 cm; node color nearest RHS 146B;

Leaf description: Narrowly ovate to broadly lanceolate; opposite; apex acute; base obtuse to truncate; margin serrate with 12 to 14 teeth per side; scaberulose adaxial and abaxial;

Leaf size: To about 8.5 cm long and 4.5 cm wide, average about 6.9 cm long and 3.0 cm wide;

Leaf color: Young adaxial nearest RHS 12D between veins and the area directly surrounding veins nearest RHS 137A, young abaxial nearest RHS 12D between veins and area directly surrounding veins between RHS 138A and RHS 137C; mature flowering stage adaxial between RHS 12D and RHS 11C between the veins with portion directly surrounding veins nearest RHS 137A, mature abaxial between RHS 12D and RHS 11D between the veins with portion directly surrounding veins nearest RHS 137A;

Veins: Reticulate; slightly recessed and glabrous adaxial, abaxial micro-puberulent and costate;

Vein color: Young adaxial nearest RHS 148C and abaxial nearest RHS 148C; mature adaxial nearest RHS N148C and abaxial nearest RHS 146D;

Petioles: Concavo-convex; sparsely puberulent adaxial and abaxial; to about 15 mm long and 2 mm across;

Petiole color: Adaxial center nearest RHS 146D, margin nearest RHS 145C; abaxial center nearest RHS 145C, margin nearest RHS 137B;

Inflorescence: In terminal capitulum; initial inflorescences semi-double with disk florets in the center and two to three layers of ray florets, later inflorescences nearly single with a single layer of imbricate ray florets; about 150 to 200 inflorescences per plant;

Flowering season: Begins flowering early July and continuing for about six weeks;

Inflorescence buds: Tubular with flat top and rounded base; with ray florets still upright—about mm tall and 20 mm across;

Bud color: Ray florets nearest RHS 146D with slight undertone of nearest RHS 151D;

Inflorescence longevity: Lasting about seven to ten days on the plant or as a cut flower; persistent;

Fragrance: Very slight, sweet;

Inflorescence size: To about 7 cm across and 3.5 cm tall;

Disk receptacle: Flattened round shape, about 8 mm across and 7 mm tall;

Receptacle color: Nearest RHS 146C;

*Ray florets.*—Between 20 and 50 per inflorescence, arranged in about 2 to 3 imbricate whorls; typically larger number of ray florets earlier in summer; lanceolate with bifid emarginate apex indented to about 1.5 mm; base attenuate to cuneate; margin entire; adaxial and abaxial surface glabrous and matte; aspect horizontal when mature; with typically two longitudinal furrows.

*Size.*—To about 30 mm long and 9.5 mm across near middle.

*Ray floret color.*—Upon initially becoming flat — adaxial nearest RHS 14A, abaxial nearest RHS 7B; near the final stage of effective inflorescence adaxial nearest RHS 13C, abaxial nearest 7C.

*Disk florets.*—About 100 per inflorescence and arrangement in typical Fibonacci spirals; tubular with exserted anthers and style.

*Size.*—To about 9 mm long and 3 mm wide at expanded style.

*Corolla tube.*—Consisting of five indistinguishable perianth or tepals; to about 6 mm long and 2 mm wide at apex.

*Tepals.*—Acute apex; fused in basal 5 mm; margin entire; glabrous; slightly lustrous adaxial and abaxial; to about 5 mm long and about 0.7 mm across at fusion; color apex adaxial and abaxial nearest RHS 17A; proximal adaxial portion nearest RHS 145D, proximal portion abaxial between RHS N144D and RHS 145C.

Reproductive organs: Ray florets: anandrous;

*Gynoecium.*—To 9 mm long; exserted.

*Style.*—Cylindrical; to about 4 mm long and 0.2 mm diameter; color nearest RHS 6D proximally and distally nearest RHS 17A.

*Stigma.*—Bifid in distal 1.5 mm; color nearest RHS 17A.

*Ovary.*—3 mm long and 1 mm across; color nearest 157A.

Reproductive organs: Disk florets: perfect;

*Gynoecium.*—To 9 mm long; exserted.

*Style.*—Cylindrical; to about 4 mm long and 0.2 mm diameter; color nearest RHS 6D proximally and distally nearest RHS 17A.

*Stigma.*—Bifid in distal 1.5 mm; color nearest RHS 17A.

*Ovary.*—3 mm long and 1 mm across; color nearest 157A.

*Androecium.*—Connate; to about 4.3 mm long.

*Anthers.*—Five; synandrous; introrse; basifixed; tube to about 2.3 mm long and 0.7 mm diameter; color nearest RHS 200B.

*Filaments.*—Five; to about 2 mm long and 0.2 mm diameter; color nearest RHS 155C.

*Pollen.*—abundant; color nearest RHS 17A.

Seeds: Achene; truncate apex; acute base; surface smooth, glabrous, matte; quadrangular distally; to about 4 mm long and 2 mm across at apex, average about 3 mm long and 1.8 mm across; about 63 per inflorescence; color nearest RHS 200A;

Flowering period: In Western Michigan beginning early July for about six weeks; individual florets remain open for about 4 to 6 days;

Flower attitude: Upwardly to slightly outwardly;

Phyllaries: About 27 per inflorescence in two whorls; lanceolate; acute apex; margin entire; puberulent and matte adaxial and abaxial; about 8 mm long and 2 mm across at base;

Phyllary color: Adaxial between RHS N137A and RHS 137A; abaxial nearest RHS 146A;

Peduncles: Cylindrical; micro-puberulent; strong; stiff; upright; to about 10.8 cm long, 2.5 mm diameter proximally and 6.0 mm diameter at base of inflorescence;

Peduncle color: Nearest RHS 146D;

Growth: The new plant has been observed to have good garden performance and tolerance to high winds and strong rains;

Hardiness: Winter hardy in USDA zones. 4 to 9;

Pest and disease susceptibility: Shows resistance to powdery mildew (*Neoerysiphe galeopsidis*) but shows no other resistance or susceptibility observed beyond that which is typical for *Heliopsis.*

I claim:

1. A new and distinct hardy perennial *Heliopsis* plant named 'Bit of Honey' essentially as herein described and illustrated.

* * * * *